United States Patent
Tong et al.

(10) Patent No.: US 10,022,365 B2
(45) Date of Patent: Jul. 17, 2018

(54) LIPOSOME OF IRINOTECAN OR IRINOTECAN HYDROCHLORIDE AND PREPARATION METHOD THEREOF

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Xinyong Tong, Shanghai (CN); Guofeng Lei, Shanghai (CN); Chengxia Yu, Shanghai (CN); Liang Chen, Shanghai (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 15/464,922

(22) Filed: Mar. 21, 2017

(65) Prior Publication Data

US 2017/0189392 A1 Jul. 6, 2017

Related U.S. Application Data

(63) Continuation of application No. 13/512,048, filed as application No. PCT/CN2009/075298 on Dec. 3, 2009, now abandoned.

(51) Int. Cl.
*A61K 9/127* (2006.01)
*A61K 31/4745* (2006.01)
(Continued)

(52) U.S. Cl.
CPC ........ *A61K 31/4745* (2013.01); *A61K 9/0019* (2013.01); *A61K 9/127* (2013.01);
(Continued)

(58) Field of Classification Search
None
See application file for complete search history.

(56) References Cited

U.S. PATENT DOCUMENTS 6,740,335 B1 * 5/2004 Moynihan ............... A61K 9/127
264/4.1
7,846,473 B2 * 12/2010 Yoshino ............. A61K 31/4745
424/450

(Continued)

FOREIGN PATENT DOCUMENTS

CN     1323199 A    11/2001
CN     1650864 A     8/2005
(Continued)

OTHER PUBLICATIONS

Qui et al in Journal of Jiangsu University, vol. 19, # 4, 2009, pp. 314-319 (English Translation).*
(Continued)

*Primary Examiner* — Gollamudi Kishore
(74) *Attorney, Agent, or Firm* — Panitch Schwarze Belisario & Nadel LLP

(57) ABSTRACT

A liposome of irinotecan or irinotecan hydrochloride and its preparation method are disclosed. The liposome contains irinotecan or irinotecan hydrochloride, neutral phospholipid and cholesterol, wherein the weight ratio of the cholesterol to the neutral phospholipid is 1:3 to 1:5. The liposome is prepared by an ion gradient method.

23 Claims, 2 Drawing Sheets

(51) Int. Cl.
  *A61K 9/00* (2006.01)
  *A61K 47/02* (2006.01)
  *A61K 47/18* (2017.01)
  *A61K 47/24* (2006.01)
(52) U.S. Cl.
  CPC ............ *A61K 9/1278* (2013.01); *A61K 47/02* (2013.01); *A61K 47/183* (2013.01); *A61K 47/24* (2013.01)

(56) References Cited

U.S. PATENT DOCUMENTS

| | | | |
|---|---|---|---|
| 2007/0116753 A1* | 5/2007 | Hong | A61K 9/0019 424/450 |
| 2009/0148506 A1* | 6/2009 | Dicko | A61K 9/1278 424/450 |

FOREIGN PATENT DOCUMENTS

| | | |
|---|---|---|
| CN | 1960729 A | 5/2007 |
| CN | 1994279 A | 7/2007 |
| CN | 101019834 A | 8/2007 |
| CN | 101283983 A | 10/2008 |
| WO | 2005117878 A1 | 12/2005 |
| WO | 2008114274 A1 | 9/2008 |

OTHER PUBLICATIONS

Yang et al in Chinese Journal of new drugs, vol. 16, # 23, pp. 1-14, 2007 (English Translation).*
The Merck Index, Oct. 1984, p. 5271.*
Int'l Search Report dated Sep. 23, 2010 in Int'l Application No. PCT/CN2009/075298.
Diu et al., "Preparation and quality evaluation of irinotecan hydrochloride lyophilized liposomes," Journal of Jiangsu University (Medical Edition), vol. 19, No. 4, pp. 314-319 (2009).
Yang et al., "Study of preparation of irinotecan hydrochloride liposomes and its influence factors," Chinese Journal of New Drugs, vol. 16, No. 23, pp. 1962-1964 (2007).

* cited by examiner

LIPOSOME OF IRINOTECAN OR IRINOTECAN HYDROCHLORIDE AND PREPARATION METHOD THEREOF

CROSS-REFERENCE TO RELATED APPLICATION

This application is continuation of U.S. application Ser. No. 13/512,048, filed on May 25, 2012, which is a Section 371 of International Application No. PCT/CN2009/075298, filed Dec. 3, 2009, which was published in the Chinese language on Jun. 9, 2011, under International Publication No. WO 2011/066684 A1. Each disclosure is incorporated herein by reference in its entirety.

FIELD OF THE INVENTION

The present invention relates to a liposome of irinotecan or its hydrochloride and preparation method thereof, and an injection comprising the said liposome and preparation method thereof.

BACKGROUND OF THE INVENTION

Irinotecan is a semi-synthetic derivative of camptothecin. Camptothecin can specifically bind to topoisomerase I, which can induce reversible DNA single-strand breaks, and then unwind the DNA double-strand structure. Irinotecan and its active metabolite SN-38 can bind to topoisomerase I-DNA complex, thereby preventing re-connection of the single-stranded fracture. It has been proved that the cytotoxicity of irinotecan can be attributed to the interaction of replicase and topoisomerase I-DNA-irinotecan (or SN-38) triple complexes, which breaks DNA double-strand in DNA synthesis.

Irinotecan hydrochloride is widely used in the treatment of malignant tumor with the advantages of obvious pharmacological effects and clinical efficacy. However, it has the same problem with other camptothecin derivatives: the saturated lactone ring in irinotecan's structure is pH-dependent and can be transformed into its carboxylate form reversibly under physiological conditions, for which anti-tumor activity will be weakened. The existing commercial formulations of irinotecan hydrochloride are liquid injection and freeze-dried powder for injection. After intravenous administration in clinical, the free drug will lose activity because the lactone ring in its structure is prone to be hydrolyzed into the carboxylate form in the alkaline physiological environment, thereby reducing drug efficacy indirectly. And these formulations have serious side effects, which are mainly neutropenia and delayed diarrhea.

Liposome is widely studied as a drug carrier in recent years. The main features of liposome include protecting the encapsulated drug, increasing drug stability, changing the in vivo distribution behavior of drug, and carrying drug to the diseased region by passive or active targeting. As a good carrier of anticancer drugs, liposome can improve drug efficacy and reduce drug toxicity.

The international application WO2005/117878 disclosed a formulation of irinotecan liposome and preparation method thereof. This formulation comprises irinotecan or irinotecan hydrochloride, phospholipid selected from the group consisting of hydrogenated soybean phosphatidylcholine, phosphatidylethanolamine, lecithin and cardiolipin, and cholesterol. Similarly, the Chinese patent application CN1994279A also disclosed a formulation of irinotecan liposome and preparation method thereof, wherein phosphatidylcholine is used as a phospholipid to prepare a liposome in Example 5.

The formulations mentioned in the above patent literatures can achieve good effect. However, when those formulations are used in human, the stability, particle size and the like are still unsatisfactory.

DESCRIPTION OF THE INVENTION

The present invention provides a liposome of irinotecan or irinotecan hydrochloride, which has higher drug-loaded capacity, high encapsulation efficiency, good stability and is suitable to be prepared into a formulation.

Up to now, some literatures (e.g., International Application WO2005/117878 and CN1994279A) have described the composition and preparation methods of irinotecan liposome. In some formulations of them some indexes had good result. However, there are no any information about stability and particle size control. After a further study for the liposome, we were surprised to find that the amount of the cholesterol in particular had an impact on the particle size and stability of the liposome when the selected type of inactive ingredient and the amount used in the formulation met some conditions. We successfully prepared a liposome with small and uniform particle size distribution and improved its stability by controlling the ratio between the neutral phospholipid and cholesterol. Compared with other formulations, the liposome of the present application has higher storage stability, and other indicators also improved significantly. In addition, compared with the technologies described in International Application WO2005/117878 and CN1994279A, these products do not comprise a compound with basic functional group and a cationic lipid. And the liposome of the present invention has good anti-tumor effect and some advantages of simple formulation, high drug-loaded capacity and good storage stability.

The liposome of the present invention comprises irinotecan or irinotecan hydrochloride, a neutral phospholipid and cholesterol, and the weight ratio of cholesterol to the neutral phospholipid is 1:3~5, preferably 1:3.5~4.5, most preferably 1:4.

The neutral phospholipid used in the present invention is selected from the group consisting of hydrogenated soybean phosphatidylcholine (HSPC), egg phosphatidylcholine (EPC), soybean phosphatidylcholine (SPC) and the like. The effect becomes the best when hydrogenated soybean phosphatidylcholine is utilized as a neutral phospholipid. The drug-loaded capacity of the liposome can be improved greatly when the weight ratio of the drug to the phospholipid is further adjusted as follows:

| Irinotecan or irinotecan hydrochloride | 1 |
|---|---|
| neutral phospholipid | 2~5, preferably 2.5-4. |

Liposome of the present invention can be prepared by conventional liposome preparation methods in the art, preferably by ion gradient method. When using ion gradient method, there is ion gradient formed by a buffer between the internal water phase and the external water phase of the said liposome. Preferably the internal water phase of the said liposome has higher ion concentration than the external water phase, which can improve the particle size stability of liposome during the storage period, maintain better drug efficacy, and be able to control the average particle size of the liposome small and uniform, enable the change in particle size of the liposome to be reduced to minimum during the storage period.

In the present invention, the change in particle size of the liposome during the storage period can be reduced to minimum by adding a lipid derivative of hydrophilic polymer to the formulation. And, the cycle time of the liposome in vivo can be extended through adding a polyethylene glycol derivative into the formulation. The polyethylene glycol derivative is selected from the group consisting of polyethylene glycol 2000-distearoyl phosphatidyl ethanolamine (DSPE-PEG$_{2000}$), polyethylene glycol 5000-distearoyl phosphatidyl ethanolamine, polyethylene glycol 2000-dipalmitoyl phosphatidyl ethanolamine, polyethylene glycol 5000-dipalmitoyl phosphatidyl ethanolamine. In order to improve the long-term efficacy of drug, a lipid derivative of hydrophilic polymer is preferred to be added to the liposome in the present invention. Based on this formulation ratio, DSPE-PEG$_{2000}$ has the most obvious effect. The preferred weight ratio of the lipid derivative to irinotecan or irinotecan hydrochloride is 0.2~0.4.

The liposome may further comprises a charged phospholipid selected from the group consisting of dilauroyl phosphatidylglycerol, dipalmitoyl phosphatidylglycerol, distearoyl phosphatidyl glycerol, dimyristate phosphatidylglycerol, dioleic acid phosphatidylserine, dioleoyl phosphatidylglycerol, dilauroyl phosphatidic acid, dimyristate phosphatidic acid, distearoyl phosphatidic acid and a mixture thereof, and the weight ratio of the charged phospholipid to the neutral phospholipid is 1:5~1:100.

Preferably, the liposome of the present invention comprises the following weight ratios of ingredients:

| | |
|---|---|
| irinotecan hydrochloride | 1 |
| hydrogenated soybean phosphatidylcholine | 3.4-3.8 |
| polyethylene glycol 2000-distearoyl phosphatidyl ethanolamine | 0.34-0.38 |
| cholesterol | 0.8-0.95, | and the ratio of cholesterol to hydrogenated soybean phosphatidylcholine is 1:4.

The present invention also provides a preparation method of the liposome of irinotecan or irinotecan hydrochloride. The liposome of the present invention can be prepared by a conventional liposome preparation method. The person skilled in the art can choose a variety of methods to prepare the liposome according to the formulation provided by the present invention. To the formulation of the liposome in the present invention, the ion gradient preparation method is preferably selected. The preparation method comprises the following steps of:

1) preparation a blank liposome by any one of the following methods A to D:

A. dissolving a neutral phospholipid and cholesterol into anhydrous ethanol or a mixed solvent of anhydrous ethanol and tert-butyl alcohol according to the desired formulation, mixing the mixture with a buffer to obtain a crude blank liposome after removing ethanol through reduced pressure distillation, and then preparing a bank liposome with the desired particle size by using high-pressure homogenizer and/or extrusion equipment;

B. dissolving a neutral phospholipid and cholesterol into chloroform or a chloroform-methanol mixed solvent according to the desired formulation, forming a lipid film through rotary evaporator, adding a buffer for hydration to obtain a crude blank liposome, and then preparing a blank liposome with the desired particle size by using high pressure homogenizer and/or extrusion equipment;

C. mixing a neutral phospholipid, cholesterol and a buffer according to the desired formulation, then preparing a blank liposome with the desired particle size by using high-pressure homogenizer and/or extrusion equipment;

D. dissolving a neutral phospholipid and cholesterol into anhydrous ethanol or a mixed solvent of anhydrous ethanol and tert-butyl alcohol according to the desired formulation, mixing the mixture with a buffer, and then preparing a blank liposome with the desired particle size by using high pressure homogenizer and/or extrusion equipment;

2) formation of ionic gradient between the internal water phase and the external water phase of the blank liposome: replacing the external water phase of the blank liposome to form ionic gradient between the internal water phase and the external water phase of the blank liposome;

3) preparation of a drug-loaded liposome: preparing an aqueous solution of irinotecan hydrochloride, adding it to the dispersion of blank liposome with ionic gradient, and then incubating the dispersion to obtain the drug-loaded liposome under heating and stirring.

After the said step 3) of preparation of a drug-loaded liposome", the said method can also comprise the following step of:

4) removal of the free drug and concentration of the sample: adding a buffer medium to irinotecan hydrochloride liposome, removing the non-encapsulated drug by using tangential flow device, and concentrating the sample to appropriate volume.

The present invention also provides a liposome injection comprising the above liposome. When a liposome is prepared to an injection suitable for human use, it's beneficial to add a stabilizer. The stabilizer used in the present invention can be a conventional stabilizer, such as vitamin E, ethylene diamine tetra acetic acid, and so on. The stabilizer is helpful for the stability of the formulation. For the formulation described above, the study on stabilizer shows that ethylene diamine tetraacetic acid or its salt has the best effect relative to other stabilizers. They are beneficial for improving the stability of the liposome. So the stabilizer can be the ethylene diamine tetraacetic acid, ethylene diamine tetraacetic acid disodium and ethylene diamine tetraacetic acid dicalcium or a mixture thereof The ratio of the stabilizer added is 0~0.5% (w/v), and the minimum is not 0%.

The composition of the present invention preferably comprises an antioxidant selected from the group consisting of water-soluble antioxidant and oil-soluble antioxidant, wherein the said oil-soluble antioxidant is selected from the group consisting of α-tocopherol, α-tocophero succinate, α-tocopherol acetate and a mixture thereof, wherein the said water-soluble antioxidant is selected from the group consisting of ascorbic acid, sodium bisulfite, sodium sulfite, sodium pyrosulfite, L-cysteine and a mixture thereof. The ratio of the antioxidant added is 0~0.5% (w/v), and the minimum is not 0%.

The injection can be in the form of liquid or lyophilized power for injection. The formulation may comprise an osmotic pressure regulator selected from the group consisting of glucose, sucrose, sorbitol, mannitol, sodium chloride, glycerine, histidine and its hydrochloride, glycine and its hydrochloride, lysine, serine, glutamic acid, arginine, valine and a mixture thereof The ratio of the osmotic pressure regulator added is 0~5% (w/v), and the minimum is not 0%.

To the formulation in the form of lyophilized power for injection, the injection further comprises a lyoprotectant, and then the injection is prepared to the Lyophilized power for injection after freeze-drying. The lyoprotectant is selected from the group consisting of glucose, sucrose, trehalose, mannitol, dextran, lactose and a mixture thereof The preferable liposome injection of the present invention comprises the following weight ratio of ingrediencies:

| irinotecan hydrochloride | 1 |
|---|---|
| hydrogenated soybean phosphatidylcholine | 3.4-3.8 |
| polyethylene glycol 2000-distearoyl phosphatidyl ethanolamine | 0.34-0.38 |
| cholesterol | 0.8-0.95 |
| ethylene diamine tetraacetic acid disodium | 0.05-0.09, | and the ratio of cholesterol to hydrogenated soybean phosphatidylcholine is 1:4.

The preparation method of the injection described above comprises the following steps of:

1) preparation of a blank liposome by any one of the following methods A to D:

A. dissolving a neutral phospholipid and cholesterol into anhydrous ethanol or a mixed solvent of anhydrous ethanol and tert-butyl alcohol according to the desired formulation, mixing the mixture with a buffer to obtain a crude blank liposome after removing ethanol through reduced pressure distillation, and then preparing a bank liposome with the desired particle size by using high-pressure homogenizer and/or extrusion equipment;

B. dissolving a neutral phospholipid and cholesterol into chloroform or a chloroform-methanol mixed solvent according to the desired formulation, forming a lipid film through rotary evaporator, adding a buffer for hydration to obtain a crude blank liposome, and then preparing a blank liposome with the desired particle size by using high pressure homogenizer and/or extrusion equipment;

C. mixing a neutral phospholipid, cholesterol and a buffer according to the desired formulation, then preparing a blank liposome with the desired particle size by using high-pressure homogenizer and/or extrusion equipment;

D. dissolving a neutral phospholipid and cholesterol into anhydrous ethanol or a mixed solvent of anhydrous ethanol and tert-butyl alcohol according to the desired formulation, mixing the mixture with a buffer, and then preparing a blank liposome with the desired particle size by using high pressure homogenizer and/or extrusion equipment;

2) formation of ionic gradient between the internal water phase and the external water phase of the blank liposome: replacing the external water phase of the blank liposome to form ionic gradient between the internal water phase and the external water phase of the blank liposome;

3) preparation of a drug-loaded liposome: preparing an aqueous solution of irinotecan hydrochloride, adding it to the dispersion of blank liposome with ionic gradient, and then incubating the dispersion to obtain the drug-loaded liposome under heating and stirring.

After the said step 3) of preparation of a drug-loaded liposome, the said method can also comprise the following step of:

4) removal of the free drug and concentrating the sample: adding a buffer medium to irinotecan hydrochloride liposome, removing the non-encapsulated drug by using tangential flow device, and concentrating the sample to appropriate volume.

After the liposome is obtained, the drug concentration is adjusted by diluting to the metered volume; the liposome is sterilized by filtration, then filled and sealed to obtain the liposome injection. Or after a lyoprotectant is added to the liposome drug sample, the drug concentration is adjusted by diluting to the metered volume, the liposome is sterilized by filtration, then filled, sealed and freeze-dried to obtain the liposome lyophilized powder for injection.

The beneficial effects of the present invention:

The liposome formulation of irinotecan or irinotecan hydrochloride has overcome many deficiencies of existing products and technologies. Drug stability can be improved by encapsulating drugs into the internal water phase of liposome. Because the drug is in the form of lactone ring in vivo, the concentration of the active metabolite SN-38 is kept for a long time in plasma. Generally speaking, the liposome formulation of irinotecan or irinotecan hydrochloride can increase the efficacy of formulation and reduce the side effects of drugs.

The liposome formulation of irinotecan or irinotecan hydrochloride of the present invention has solved the problem of low drug-loaded capacity in liposome by controlling the specific ratio between drug, phospholipid and cholesterol. The ratio of drug to lipid in the liposome injection is over 0.25 (w/w), and the encapsulation efficiency is over 90%, preferably over 95%. The liposome prepared by the present invention has smaller particle size and improves the stability by optimizing the dosage of cholesterol and phospholipid. By screening the stabilizer, a certain percentage of ethylene diamine tetraacetic acid salts is preferably added to the formulation to improve the stability of the liposome significantly, and the particle size distribution of the liposome is uniformly in the range of 10 nm~220 nm. The results of the influencing factor experiment of liposome injection of irinotecan or irinotecan hydrochloride show that the particle size and encapsulation efficiency of the sample has no significant change when placed at 40° C. for 10 days, and indexes all meet the requirements. Compared with commercially available formulations, the liposome injection of irinotecan or irinotecan hydrochloride has a significant increase in tumor inhibitory rate and a significant reduce in its toxicity.

PREFERRED EMBODIMENTS

Figure 1:
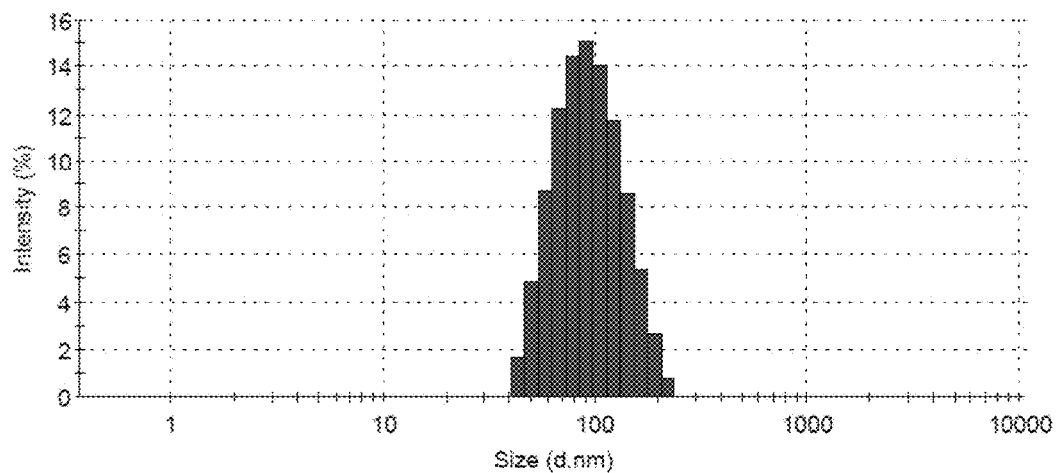
FIG. 1 shows the particle size distribution of liposome injection of irinotecan or irinotecan hydrochloride according to the present invention.

The following examples are intended to further illustrate the invention, but are in no way intended to limit the scope thereof.

EXAMPLE 1

Formulation:

| irinotecan hydrochloride | 0.28 g | 0.28 g | 0.28 g | 0.28 g | 0.28 g |
|---|---|---|---|---|---|
| hydrogenated soybean phosphatidylcholine | 1 g | 1 g | 1 g | 1 g | 1 g |
| cholesterol | 0.4 g | 0.33 g | 0.25 g | 0.2 g | 0.167 g |
| DSPE-PEG2000 | 0.1 g | 0.1 g | 0.1 g | 0.1 g | 0.1 g |

-continued

| | | | | | |
|---|---|---|---|---|---|
| ammonium sulfate | 5 g | 5 g | 5 g | 5 g | 5 g |
| sodium chloride | 0.45 g | 0.45 g | 0.45 g | 0.45 g | 0.45 g |
| cholesterol:phospholipid | 1:2.5 | 1:3 | 1:4 | 1:5 | 1:6 |
| injectable water | up to the required volume | | | | |

Preparation Method: ydrogenated soybean phosphatidylcholine (HSPC) and cholesterol (CHOL) of the formulation amount were dissolved in an adequate amount of anhydrous ethanol, the resulting lipid solution was mixed with ammonium sulfate solution (100 ml), ethanol was removed by reduced pressure distillation, and then the crude blank liposome was obtained. After 5 cycles homogenization in high-pressure homogenizer (1000 bar), the particle size of liposome was controlled by extruding the liposome on extrusion equipment (two 0.1 μm extrusion membranes on extrusion equipment, five times extrusion), and then DSPE-PEG$_{2000}$ aqueous solution was added. Under stirring, the mixture was incubated for 20 minutes. The blank liposome was dialyzed by using tangential flow ultrafiltration device with continuous supplementary of injectable water in the course, then the blank liposome was obtained finally.

Irinotecan hydrochloride aqueous solution was prepared with injectable water and was added to the dispersion of blank liposome with ion gradient above according to the weight ratio of irinotecan hydrochloride to HSPC 1:3.5. Under stirring, the mixture was heated to 60° C. and incubated for 20 minutes, and then the drug-loaded liposome was obtained. The non-encapsulated drug was removed by using tangential flow ultrafiltration device. 0.45 g sodium chloride was added to adjust the osmotic pressure after the sample was concentrated to about 50 ml. After the drug concentration was adjusted by diluting to the metered volume, the liposome was sterilized by filtration with 0.22 μm filter, filled under the protection of nitrogen, and sealed in a small bottle. The liposome injection of irinotecan hydrochloride was obtained finally.

The change in particle size of each formulation was shown in the table below. The results indicated that the particle size of the sample was the smallest when the weight ratio of phospholipid to cholesterol was 4:1.

| HSPC:CHOL | Preparation procedure | Average particle size |
|---|---|---|
| 6:1 | After homogenization | 138.7 |
| | 0.1 μm five times extrusion | 92.26 |
| 5:1 | After homogenization | 136.2 |
| | 0.1 μm five times extrusion | 89.5 |
| 4:1 | After homogenization | 123.4 |
| | 0.1 μm five times extrusion | 87.26 |
| 3:1 | After homogenization | 145.1 |
| | 0.1 μm five times extrusion | 93.4 |
| 2.5:1 | After homogenization | 142 |
| | 0.1 μm five times extrusion | 98.56 |

The stability of the sample prepared was investigated at 25° C. at various weight ratios of phospholipid to cholesterol. The results were shown in the table below. After stored at 25° C. for 60 days, the particle size and encapsulation efficiency of the sample had no significant changes when the weight ratio of phospholipid to cholesterol was 4:1. However, for the samples having other weight ratios of phospholipid to cholesterol, the size of the sample increased and the encapsulation efficiency declined. Therefore, the stability of the sample was better when the weight ratio of phospholipid to cholesterol was 4:1.

| HSPC:CHOL | Storage time (25° C., day) | Appearance | Encapsulation efficiency % | Particle size (z-v) nm | Potential (mv) | Content (mg/ml) | Total impurities % | Lysophospholipid (mg/ml) |
|---|---|---|---|---|---|---|---|---|
| 6:1 | 0 | Off-white suspension | 98.86 | 92.3 | −30.5 | 5.05 | 0.58 | 0.39 |
| | 30 | Off-white suspension | 98.56 | 94.3 | −26.8 | 5.04 | 0.75 | 0.56 |
| | 60 | Off-white suspension | 98.20 | 95.9 | −24.9 | 5.06 | 0.85 | 0.66 |
| 4:1 | 0 | Off-white suspension | 99.37 | 87.3 | −32.1 | 5.10 | 0.55 | 0.40 |
| | 30 | Off-white suspension | 99.25 | 87.5 | −30.9 | 5.11 | 0.64 | 0.50 |
| | 60 | Off-white suspension | 99.18 | 87.8 | −28.6 | 5.09 | 0.70 | 0.62 |
| 2.5:1 | 0 | Off-white suspension | 99.27 | 98.5 | −35.8 | 5.12 | 0.60 | 0.38 |
| | 30 | Off-white suspension | 98.75 | 100.2 | −28.6 | 5.09 | 0.73 | 0.51 |
| | 60 | Off-white suspension | 98.19 | 101.7 | −25.3 | 5.07 | 0.84 | 0.67 |

Conclusions: Taking into account all the indexes, it can obtain better results when the ratio of cholesterol to phospholipid was 1:3~5, most preferably 1:4.

EXAMPLE 2

Formulation:

| | |
|---|---|
| irinotecan hydrochloride | 0.28 g |
| hydrogenated soybean phosphatidylcholine (HSPC) | 1 g |
| polyethylene glycol 2000-distearoyl phosphatidylethanolamine (DSPE-PEG$_{2000}$) | 0.1 g |
| cholesterol | 0.25 g |
| ammonium sulfate | 5 g |

-continued

| ethylene diamine tetraacetic acid disodium | 0.02 g |
| sodium chloride | 0.45 g |
| injectable water | up to the required volume |

Preparation Method:

Hydrogenated soybean phosphatidylcholine and cholesterol of the formulation amount were dissolved in an adequate amount of anhydrous ethanol, the resulting lipid solution was mixed with ammonium sulfate solution (100 ml), anhydrous ethanol was removed by reduced pressure distillation, and then the crude blank liposome was obtained. After 5 cycles homogenization in high-pressure homogenizer (1000 bar), the particle size of liposome was controlled by extruding the liposome on extrusion equipment (two 0.1 μm extrusion membrane on extrusion equipment, five times extrusion), and then DSPE-PEG$_{2000}$ aqueous solution was added. Under stirring, the mixture was incubated for 20 minutes. The blank liposome was dialyzed by using tangential flow ultrafiltration device with continuous supplementary of injectable water in the course, then the blank liposome was obtained finally.

Irinotecan hydrochloride aqueous solution was prepared with injectable water and was added to the dispersion of blank liposome with ion gradient above according to the weight ratio of irinotecan hydrochloride to HSPC 1:3.5. Under stirring, the mixture was heated to 60° C. and incubated for 20 minutes, and then the drug-loaded liposome was obtained. The non-encapsulated drug was removed by using tangential flow ultrafiltration device. 0.45 g sodium chloride was added to adjust the osmotic pressure after the sample was concentrated to about 50 ml. After the drug concentration was adjusted by diluting to the constant volume, the liposome was sterilized by filtration with 0.22 μm filter, filled under the protection of nitrogen, and sealed in a small bottle. The liposome injection of irinotecan hydrochloride was obtained finally.

EXAMPLE 3

The formulation and preparation method of blank liposome were as same as Example 2, except that the weight ratio of irinotecan hydrochloride to HSPC was 1:1.5, 1:2, 1:3.5, 1:4 and 1:5 in the liposome preparing process. The encapsulation efficiency and particle size of liposome sample of irinotecan hydrochloride were shown in the table below:

| CPT11:HSPC | Encapsulation efficiency (%) | Drug-loaded content (mg/ml) | Particle size (nm) |
| --- | --- | --- | --- |
| 1:1.5 | 83.2 | 5.11 | 87.1 |
| 1:2 | 90.8 | 5.15 | 86.5 |
| 1:3.5 | 99.4 | 5.08 | 85.9 |
| 1:4 | 99.1 | 4.81 | 85.4 |
| 1:5 | 99.4 | 4.25 | 86.7 |

It was shown that the encapsulation efficiency significantly reduced when the weight ratio of irinotecan hydrochloride to HSPC was 1:1.5, and the drug-loaded content decreased remarkably when the ratio was 1:5. It's not suitable for preparing formulations used in clinical application in both conditions. The encapsulation efficiency and drug-loaded content were higher when the ratio was 1:2~1:4.

EXAMPLE 4

The formulation and preparation method of blank liposome and drug-loaded liposome were as same as Example 2, except that HSPC in the formulation was replaced by high-purity egg phosphatidylcholine (EPC), high purity soybean phosphatidylcholine (SPC) respectively. The stability of resulting liposome sample was investigated at 25° C. and the results were shown in the table below. The test results showed that the stability of liposome sample prepared by HSPC was the best and the main indexes had no remarkable change when stored at 25° C. for 2 months.

| Time | PC Composition | Encapsulation efficiency (%) | Drug-loaded content (mg/ml) | Particle size (nm) |
| --- | --- | --- | --- | --- |
| 0 M | HSPC | 99.4 | 5.08 | 85.9 |
| | EPC | 99.5 | 5.10 | 87.5 |
| | SPC | 99.2 | 5.01 | 86.9 |
| 1 M | HSPC | 99.5 | 5.10 | 85.5 |
| | EPC | 92.4 | 5.07 | 88.2 |
| | SPC | 93.9 | 5.05 | 87.3 |
| 2 M | HSPC | 98.7 | 5.07 | 86.5 |
| | EPC | 85.8 | 5.06 | 93.2 |
| | SPC | 89.6 | 5.02 | 91.5 |

EXAMPLE 5

Formulation:

| irinotecan hydrochloride | 0.28 g |
| hydrogenated soybean phosphatidylcholine (HSPC) | 1 g |
| polyethylene glycol 2000-distearoyl phosphatidylethanolamine (DSPE-PEG$_{2000}$) | 0.1 g |
| cholesterol | 0.25 g |
| saline solution | 50 ml |
| injectable water | up to the required volume |

Preparation Method <1>:

Ethanol injection method: hydrogenated soybean phosphatidylcholine, DSPE-PEG$_{2000}$ and cholesterol of the formulation amount were dissolved in an adequate amount of anhydrous ethanol, the resulting lipid solution was injected into saline solution of irinotecan hydrochloride. Ethanol was removed by reduced pressure distillation, and then the crude blank liposome was obtained. The particle size of the liposome was controlled by extruding the liposome on extrusion equipment (two 0.1 μm extrusion membrane on extrusion equipment, five times extrusion) after 5 cycles homogenization in high-pressure homogenizer (1000 bar). The drug concentration was adjusted by diluting to metered volume, the liposome was sterilized by filtration with 0.22 μm filter, filled under the protection of nitrogen, and sealed in a small bottle. The liposome injection of irinotecan hydrochloride was obtained finally.

Preparation Method <2>:

Film dispersion method: hydrogenated soybean phosphatidylcholine, DSPE-PEG$_{2000}$ and cholesterol of the formulation amount were dissolved in an adequate amount of chloroform and the resulting lipid solution was prepared to film by rotary evaporator then the chloroform was removed. Saline solution of irinotecan hydrochloride was added and the mixture was incubated for 1 h. The particle size of the liposome was controlled by extruding the liposome on extrusion equipment (two 0.1 μm extrusion membrane on extrusion equipment, five times extrusion) after 5 cycles homogenization in high-pressure homogenizer (1000 bar). The drug concentration was adjusted by diluting to metered volume, the liposome was sterilized by filtration with 0.22 μm filter, filled under the protection of nitrogen, and sealed in a small bottle. The liposome injection of irinotecan hydrochloride was obtained finally.

The encapsulation efficiency and particle size of the irinotecan hydrochloride liposome prepared by Preparation method <1>, <2> and Example 2 were determined.

| Sample | Encapsulation efficiency (%) | Particle size (nm) |
| --- | --- | --- |
| Example 2 | 99.4 | 85.9 |
| Preparation method <1> | 15.3 | 87.9 |
| Preparation method <2> | 17.8 | 90.2 |

It was shown that the target product could be prepared by passive drug-loaded methods such as ethanol injection method and film dispersion method when preparing liposome of irinotecan hydrochloride. But the liposome prepared by these methods had low encapsulation efficiency and only a small amount of the drug can be loaded into the liposome. In contrast, the sample prepared by active drug-loaded method (Example 2) had high encapsulation efficiency and drug-loaded content. In addition, the sample prepared by active drug-loaded method had small and uniform particle size. So in the present invention, the active drug-loaded method was used to prepare the liposome. It had extremely good results to prepare the liposome of irinotecan hydrochloride by ion gradient method.

EXAMPLE 6

| Formulation | Formulation 1 | Formulation 2 | Formulation 3 | Formulation 4 |
| --- | --- | --- | --- | --- |
| HSPC | 1 g | 1 g | 1 g | 1 g |
| Cholesterol | 250 mg | 250 mg | 250 mg | 250 mg |
| $PEG_{2000}$-DSPE | 0.1 g | 0.1 g | 0.1 g | 0.1 g |
| Vitamin E | / | 0.02 g | / | 0.02 g |
| EDTA-2Na | / | / | 0.02 g | 0.02 g |
| Ammonium sulfate solution (300 mM) | 100 ml | 100 ml | 100 ml | 100 ml |
| Irinotecan hydrochloride | 0.3 g | 0.3 g | 0.3 g | 0.3 g |

Preparation Method:

Blank liposome: the lipid ethanol solution was injected, and the solution was homogenized under 1000 bar, 6 times; extruded 3 times in 200 nm, 5 times in 100 nm; $PEG_{2000}$-DSPE was added and the mixture was incubated for 30 min at 60° C. Then the mixture was dialyzed 3 times with tangential flow device, 50 ml every time, wherein Vitamin E(VE) was added to phospholipid organic solvent and EDTA was added to ammonium sulfate solution.

Drug-loaded liposome: about 10 mg/ml of irinotecan hydrochloride aqueous solution was prepared and added to the blank liposome, then the mixture was incubated at 60° C. for 15 min. The sample was concentrated to approximately 50 ml by using tangential flow device and 5 mg/ml of sample was obtained.

The results of stability were shown in the table below. All indexes of the sample had no remarkable change when EDTA was added alone. It improved the stability of the liposome significantly. But other stabilizers did not significantly improve the stability of the liposome.

| Sample | Storage time (25° C., day) | Appearance | Encapsulation efficiency % | Particle size (z-v) nm | Content mg/ml | Total impurities % | Lysophospholipid (mg/ml) |
| --- | --- | --- | --- | --- | --- | --- | --- |
| HSPC | 0 | Off-white suspension | 99.70 | 85.6 | 5.42 | 0.65 | 0.40 |
|  | 30 | Off-white suspension | 91.51 | 87.7 | 5.40 | 0.74 | 0.65 |
| HSPC + VE | 0 | Off-white suspension | 97.10 | 89.0 | 5.01 | 0.48 | 0.35 |
|  | 30 | Off-white suspension | 93.49 | 93.4 | 5.03 | 0.56 | 0.43 |

| Sample | Storage time (25° C., day) | Appearance | Encapsulation efficiency % | Particle size (z-v) nm | Content mg/ml | Total impurities % | Lysophospholipid (mg/ml) |
|---|---|---|---|---|---|---|---|
| HSPC + EDTA | 0 | Off-white suspension | 95.67 | 87.2 | 4.94 | 0.56 | 0.38 |
|  | 30 | Off-white suspension | 95.67 | 86.5 | 4.98 | 0.60 | 0.40 |
| HSPC + VE + EDTA | 0 | Off-white suspension | 98.92 | 89.2 | 5.55 | 0.61 | 0.39 |
|  | 30 | particle precipitation | 87.31 | 99.7 | 5.51 | 0.61 | 0.47 |

EXAMPLE 7

Formulation (1):

| | |
|---|---|
| irinotecan hydrochloride | 0.5 g |
| hydrogenated soybean phosphatidylcholine | 1.5 g |
| cholesterol | 0.4 g |
| manganese sulfate | 10 g |
| mannitol | 2.5 g |
| injectable water | up to the required volume |

Preparation Method:

Hydrogenated soybean phosphatidylcholine and cholesterol of the formulation amount were dissolved in an adequate amount of anhydrous ethanol and the resulting lipid solution was mixed with manganese sulfate solution (100 ml). After anhydrous ethanol was removed by reduced pressure distillation, the crude blank liposome was obtained. The particle size of the liposome was controlled by extruding the liposome on extrusion equipment (two 0.1 μm extrusion membrane on extrusion equipment, five times extrusion). The blank liposome was dialyzed by using tangential flow ultrafiltration device with continuous supplementary of injectable water in the course, then the blank liposome was obtained. Irinotecan hydrochloride aqueous solution was prepared with injectable water and was added to the dispersion of blank liposome with ion gradient. Under stirring, the mixture was heated to 50° C. and incubated for 20 minutes, and then the drug-loaded liposome was obtained. The non-encapsulated drug was removed by using tangential flow ultrafiltration device and then 2.5 g mannitol was added to adjust the osmotic pressure. After the drug concentration was adjusted by diluting to the constant volume, the liposome was sterilized by filtration with 0.22 μm filter, and then filled under the protection of nitrogen, and sealed in a small bottle. The liposome injection of irinotecan hydrochloride was obtained finally. The particle size of the liposome was measured by the nano particle size analyzer (89.3 nm), and the encapsulation efficiency was 97.5%.

Formulation (2):

| | |
|---|---|
| irinotecan hydrochloride | 1 g |
| hydrogenated egg lecithin (HEPC) | 3.45 g |
| cholesterol | 0.8 g |
| magnesium sulfate | 10 g |
| histidine | 2.5 g |
| injectable water | up to the required volume |

Preparation Method:

Hydrogenated egg lecithin and cholesterol of the formulation amount were dissolved in an adequate amount of anhydrous ethanol and the resulting lipid solution was mixed with manganese sulfate solution (100 ml). The particle size of the liposome was controlled by extruding the liposome on extrusion equipment (two 0.1 μm extrusion membrane on extrusion equipment, five times extrusion). The blank liposome was dialyzed by using tangential flow ultrafiltration device with continuous supplementary of injectable water in the course, then the blank liposome was obtained. Irinotecan hydrochloride aqueous solution was prepared with injectable water and was added to the dispersion of blank liposome with ion gradient. Under stirring, the mixture was heated to 50° C. and incubated for 20 minutes, and then the drug-loaded liposome was obtained. The non-encapsulated drug was removed by using tangential flow ultrafiltration device and the sample was concentrated to about 50 ml. Then 2.5 g histidine was added to adjust the osmotic pressure. After the drug concentration was adjusted by diluting to the metered volume, the liposome was sterilized by filtration with 0.22 μm filter, and then filled under the protection of nitrogen, and sealed in a small bottle. The liposome injection of irinotecan hydrochloride was obtained finally. The particle size of the liposome was measured by the nano particle size analyzer (87.6 nm), and the encapsulation efficiency was 98.1%.

Formulation (3):

| | |
|---|---|
| irinotecan hydrochloride | 0.3 g |
| hydrogenated soybean phosphatidylcholine (HSPC) | 1 g |
| polyethylene glycol 2000-distearoyl phosphatidylethanolamine (DSPE-PEG$_{2000}$) | 0.05 g |
| cholesterol | 0.25 g |
| ammonium sulfate | 5 g |
| sodium chloride | 0.45 g |
| injectable water | up to the required volume |

Preparation Method:

Hydrogenated soybean phosphatidylcholine and cholesterol of the formulation amount were dissolved in an adequate amount of anhydrous ethanol and the resulting lipid solution was mixed with ammonium sulfate solution (100 ml). After anhydrous ethanol was removed by reduced pressure distillation, the crude blank liposome was obtained. After 5 cycles homogenization in high-pressure homogenizer (1000 bar), DSPE-PEG$_{2000}$ aqueous solution was added. Under stirring, the mixture was incubated for 20 minutes. The blank liposome was dialyzed by using tangential flow ultrafiltration device with continuous supplementary of injectable water in the course, then the blank liposome was obtained. Irinotecan hydrochloride aqueous solution was prepared with injectable water and was added to the dispersion of blank liposome with ion gradient. Under stirring, the mixture was heated to 60° C. and incubated for 20 minutes, and then the drug-loaded liposome was obtained. The non-encapsulated drug was removed by using tangential flow ultrafiltration device and the sample was concentrated to about 50 ml. Then 0.45 g sodium chloride was added to adjust the osmotic pressure. After the drug concentration was adjusted by diluting to the metered volume, the liposome was sterilized by filtration with 0.22 μm filter, and then filled under the protection of nitrogen, and sealed in a small bottle. The liposome injection of irinotecan hydrochloride was obtained finally. The particle size of the liposome was measured by the nano particle size analyzer (87.3 nm), and the encapsulation efficiency was 99.2%.

EXAMPLE 8

Formulation:

| | |
|---|---|
| irinotecan hydrochloride | 0.5 g |
| hydrogenated soybean phosphatidylcholine (HSPC) | 1 g |
| myocardial phospholipids (CL) | 0.5 g |
| polyethylene glycol 5000-distearoyl phosphatidylethanolamine (DSPE-PEG$_{5000}$) | 0.5 g |
| α-Tocopherol | 0.05 g |
| cholesterol | 0.35 g |
| citric acid | 5.76 g |
| sodium chloride | about 3.6 g |
| injectable water | up to the required volume |

Preparation Method:

Hydrogenated soybean phosphatidylcholine, myocardial phospholipid, DSPE-PEG$_{5000}$, cholesterol and α-tocopherol of the formulation amount were dissolved in an adequate amount of anhydrous ethanol and the resulting lipid solution was mixed with citric acid solution (100 ml). After anhydrous ethanol was removed by reduced pressure distillation, the crude blank liposome was obtained. After 5 cycles homogenization in high-pressure homogenizer (1000 bar), the blank liposome was dialyzed by using tangential flow ultrafiltration device with continuous supplementary of sodium chloride solution (0.9%, 400 ml) in the course, then the blank liposome was obtained. Irinotecan hydrochloride aqueous solution was prepared with injectable water and was added to the dispersion of blank liposome with ion gradient. Under stirring, the mixture was heated to 60° C. and incubated for 20 minutes, and then the drug-loaded liposome was obtained. The non-encapsulated drug was removed by using tangential flow ultrafiltration device and the sample was concentrated to about 50 ml. After the drug concentration was adjusted by diluting to the constant volume, the liposome was sterilized by filtration with 0.22 μm filter, and then filled under the protection of nitrogen, and sealed in a small bottle. The liposome injection of irinotecan hydrochloride was obtained finally. The particle size of the liposome was measured by the nano particle size analyzer (85.8 nm), and the encapsulation efficiency was 98.6%.

EXAMPLE 9

Formulation:

| | |
|---|---|
| irinotecan hydrochloride | 0.8 g |
| dipalmitoyl phosphatidyl choline (DPPC) | 2 g |
| dipalmitoyl phosphatidylglycerol (DPPG) | 0.2 g |
| cholesterol | 0.5 g |
| ascorbic acid | 0.05 g |
| ethylene diamine tetraacetic acid disodium | 0.05 g |
| ammonium sulfate | 5 g |
| sodium chloride | about 3.6 g |
| injectable water | up to the required volume |

Preparation Method:

DPPC, DPPG and cholesterol of the formulation amount were dissolved in an adequate amount of anhydrous ethanol and the resulting lipid solution was mixed with ammonium sulfate solution (100 ml, containing ethylene diamine tetraacetic acid disodium). After ethanol was removed by reduced pressure distillation, the crude blank liposome was obtained. After 5 cycles homogenization in high-pressure homogenizer (1000 bar), the blank liposome was dialyzed by using tangential flow ultrafiltration device with continuous supplementary of sodium chloride solution (0.9%, 400 ml) in the course, then the blank liposome was obtained. Irinotecan hydrochloride aqueous solution was prepared with injectable water and was added to the dispersion of blank liposome with ion gradient. Under stirring, the mixture was heated to 60° C. and incubated for 20 minutes, and then the drug-loaded liposome was obtained. The non-encapsulated drug was removed by using tangential flow ultrafiltration device and the sample was concentrated to about 50 ml. After the drug concentration was adjusted by diluting to the constant volume, the liposome was sterilized by filtration with 0.22 μm filter, and then filled under the protection of nitrogen, and sealed in a small bottle. The liposome injection of irinotecan hydrochloride was obtained finally. The particle size of the liposome was measured by the nano particle size analyzer (89.4nm), and the encapsulation efficiency was 97.2%.

EXAMPLE 10

Formulation:

| | |
|---|---|
| irinotecan hydrochloride | 0.5 g |
| hydrogenated soybean phosphatidylcholine (HSPC) | 1 g |
| polyethylene glycol 5000-distearoyl phosphatidylethanolamine (DSPE-PEG$_{5000}$) | 0.1 g |
| α-tocopherol | 0.05 g |
| cholesterol | 0.3 g |
| ammonium sulfate | 5 g |
| sodium chloride | about 3.6 g |
| sucrose | 2 g |
| mannitol | 1 g |
| injectable water | up to the required volume |

Preparation Method:

Hydrogenated soybean phosphatidylcholine, cholesterol and α-tocopherol of the formulation amount were dissolved in an adequate amount of anhydrous ethanol and the resulting lipid solution was mixed with ammonium sulfate solution (100 ml). After ethanol was removed by reduced pressure distillation, the crude blank liposome was obtained.

After 5 cycles homogenization in high-pressure homogenizer (1000 bar), the liposome was extruded on extrusion equipment (five 100 nm extrusion membrane on extrusion equipment, five times extrusion). Then DSPE-PEG$_{5000}$ aqueous solution was added, and the mixture was incubated under stirring for 20 minutes. The blank liposome was dialyzed by using tangential flow ultrafiltration device with continuous supplementary of sodium chloride solution (0.9%, 400 ml) in the course, then the blank liposome was obtained. Irinotecan hydrochloride aqueous solution was prepared with injectable water and was added to the dispersion of blank liposome with ion gradient. Under stirring, the mixture was heated to 60° C. and incubated for 20 minutes, and then the drug-loaded liposome was obtained. The non-encapsulated drug was removed by using tangential flow ultrafiltration device and the sample was concentrated to about 50 ml. Then sucrose and mannitol were added to the mixture and mixed homogeneously. After the drug concentration was adjusted by diluting to the constant volume, the liposome was sterilized by filtration with 0.22 μm filter, and then filled into penicillin bottle and freeze-dried. The liposome lyophilized powder for injection of irinotecan hydrochloride was obtained finally. The particle size of the liposome was measured (90.8 nm) after hydration of the lyophilized powder for injection, and the encapsulation efficiency was 97.5%.

Experiment 1

Taking the product of Example 2 as an example to study the physicochemical characteristics of the product obtained according to the present invention:

taining 1% triethylamine)=20:80; column temperature: 40° C.; injection volume: 20 μL; flow rate: 1.0 mL/min.

Method for detecting encapsulation efficiency:

1 mL sample solution was pipeted into a 10 mL volumetric flask and was diluted with water to the mark. Then it was shaken homogeneously and ultrafiltered with 8010 ultrafilter (MILLIPORE company). The initial filtrate was discarded and the subsequent filtrate was reserved as the sample solution. 20 μL solution of the sample and the control were pipeted into liquid chromatography and the chromatogram was recorded. The free drug content of the formulation was calculated by external standardization method, recorded as W. The total amount of drug in this product was calculated by a content determination method, recorded as $W_0$. The encapsulation efficiency was calculated by the follow equation:

$$\text{Encapsulation Efficiency} = \frac{W_0 - W}{W_0} \times 100\%$$

Results of the determination: The encapsulation efficiency of the product was 99.4%.

[Impact Factors Test]: The impact factors were investigated by placing the product under different conditions. The results were shown in the table below:

| Conditions | Storage time (day) | Appearance | pH | Particle size (nm) | Content (%) | Encapsulation efficiency (%) | Total impurities (%) | Lysophospholipid (mg/ml) |
|---|---|---|---|---|---|---|---|---|
| Illumination 4500 lx ± 500 lx | 0 | Off-white suspension | 6.39 | 85.9 | 98.14 | 99.40 | 0.43 | 0.19 |
| | 5 | Earth yellow suspension | 6.30 | 86.3 | 78.99 | 99.11 | 14.4 | 0.23 |
| | 10 | Earth yellow suspension | 6.40 | 86.5 | 76.39 | 99.20 | 19.5 | 0.30 |
| 40° C. | 0 | Off-white suspension | 6.39 | 85.9 | 98.14 | 99.40 | 0.43 | 0.19 |
| | 5 | Off-white suspension | 6.35 | 87.1 | 98.77 | 99.29 | 0.45 | 0.29 |
| | 10 | Off-white suspension | 6.47 | 88.7 | 98.86 | 96.82 | 0.55 | 0.44 |
| Low temperature | 3 cycles | Off-white suspension | 6.41 | 89.1 | 100.07 | 99.16 | 0.44 | 0.38 |
| Freeze-thaw | 3 cycles | White suspension | 6.38 | 110.5 | 95.22 | 99.28 | 0.46 | 0.23 |

[Particle size distribution]: Appropriate amount of the sample was diluted with water then measured by Dynamic Light Scattering (DLS) method. Detective wavelength: λ=633 nm; detective angle: 173°; detective temperature: 25° C. The particle size was represented by intensity. The particle size distribution was shown in FIG. 1. The average particle size was 85.9 nm.

Figure 2:
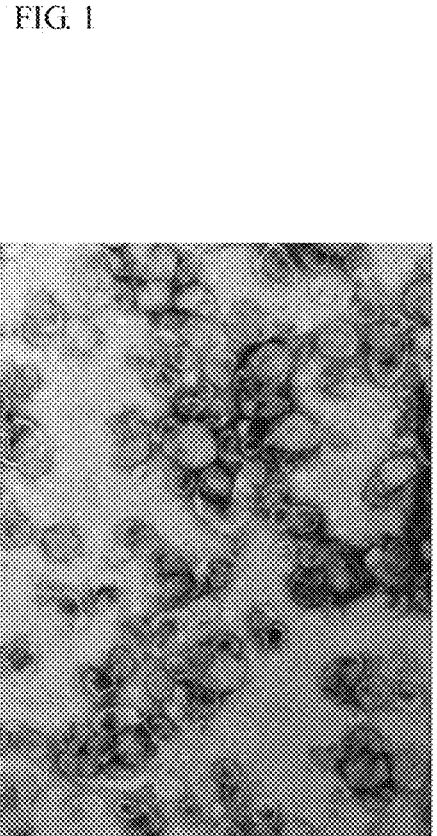
FIG. 2 shows the morphology of liposome injection of irinotecan or irinotecan hydrochloride according to the present invention.

[Morphology]: Appropriate amount of the diluted sample was drawn, a copper mesh was placed on a clean filter paper, the sample was dropped onto the copper mesh, dyed with phosphotungstic acid, and observed with transmission electron microscope (TEM, JEM2010, Japan Electronics Co., Ltd.) after dry. The morphology was shown in FIG. 2. The appearance of irinotecan hydrochloride liposome was typical bilayer structure and the majority of the particle size was below 200 nm. It's consistent with the result measured by dynamic light scattering.

[Encapsulation efficiency]: Method for determination of drug content: Column: Agilent ZORBAX Eclipse XDB-C18 (4.6×150 mm, 5 μm) mobile phase: acetonitrile –0.05M KH$_2$PO$_4$ buffer solution (pH value was adjusted to 4, con- The result was shown that the sample was light-sensitive. Under a bright light, the appearance of the sample turned yellow, the content decreased and related substances were significantly increased. The encapsulation efficiency and particle size of the sample had no remarkable change at 40° C., while related substances were increased a little. Big size particles were generated in the sample under low temperature or freeze-thaw conditions. Considering the instability of the phospholipid under high temperature and the test results of the impact factors test, the product should be stored under low-temperature and dark conditions.

[Antitumor Therapeutic Efficacy Test In Vivo]

Drug name: The liposome of Irinotecan hydrochloride (CPT-11 liposome) (prepared according to Example 2) was provided by Shanghai Hengrui Pharmaceutical Co., LTD. The injection of Irinotecan hydrochloride (CPT-11) was provided by Jiangsu Hengrui Medicine Co., LTD.

Preparation methods: The drug was diluted with saline solution to required concentration.

Experimental animals: BALB/cA-nude mice, 6-7 weeks, ♀, purchased from Shanghai Slac Laboratory Animal Co., LTD. Certificate No.: SCXK (Shanghai) 2007-0005. Environment: SPF level.

Experimental Protocol:

Nude mice were subcutaneously inoculated Ls-174t human colon cancer cell. After tumors grew to the 150-300 mm³, mice were randomly divided into teams (d0). Dosage and dosage regimens were shown in the table below. The volume of tumors and the weight of the mice were measured and recorded for 2-3 times per week. The tumor volume (V) was calculated by the follow equation:

$$V = \frac{1}{2} \times a \times b^2 \text{ wherein } a, b \text{ represent length and width respectively.}$$

| Drug | Administration | Route | Average tumor volume (mm³) D0 | SD | Average tumor volume (mm³) D12 | SD | RTV D12 | SD | % T/C D12 | Tumor inhibition rate (%) D12 | P value D12 | Partial regression | Number of animals |
|---|---|---|---|---|---|---|---|---|---|---|---|---|---|
| Vehicle | D0, 3 | IV | 219.8 | ±37.2 | 2013.7 | ±303.1 | 9.4 | ±2.3 | 100 | 0 | — | 0 | 8 |
| CPT-11 liposomes 1.0 mg/kg | D0, 3 | IV | 212.2 | ±42.1 | 732.2 | ±162.6 | 3.5 | ±0.7 | 38 | 62 | 0.000 | 0 | 13 |
| CPT-11 liposomes 3.0 mg/kg | D0, 3 | IV | 205.0 | ±49.0 | 265.1 | ±122.9 | 1.3 | ±0.4 | 13 | 87 | 0.000 | 4 | 13 |
| CPT-11 10 mg/kg | D0, 3 | IV | 204.6 | ±44.7 | 844.4 | ±197.5 | 4.2 | ±0.9 | 45 | 55 | 0.000 | 0 | 14 |

D0: the first administration time;
RTV: relative tumor volume;
P value means relative to the control.
Control group n = 12, treatment group n = 6.

Figure 3:
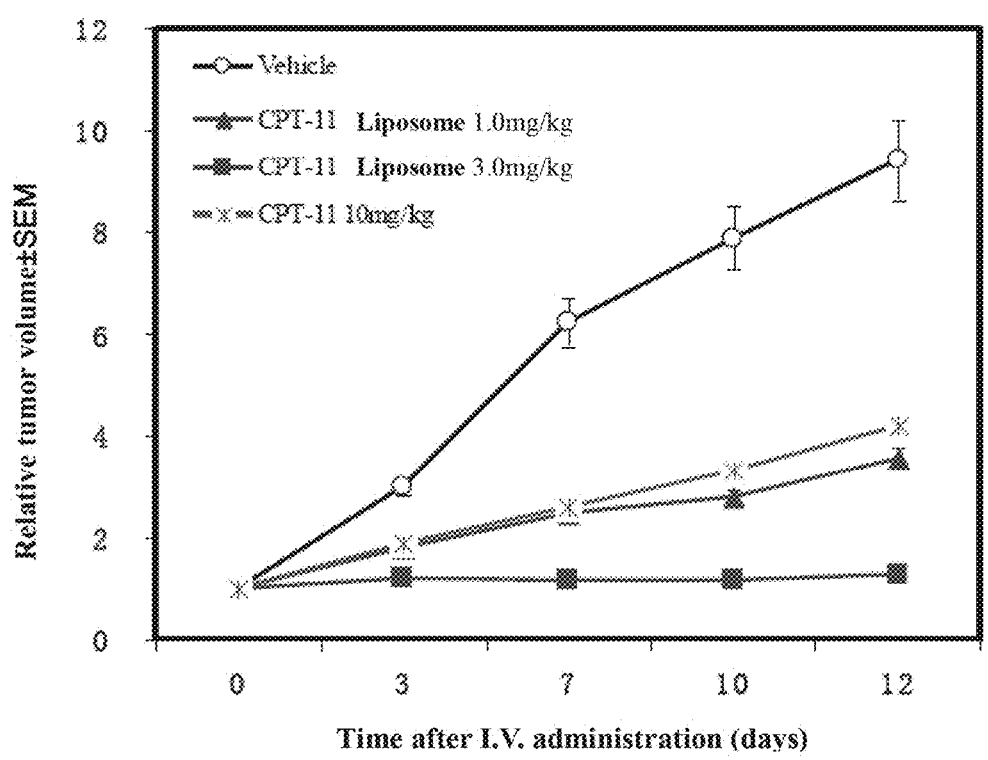
FIG. 3 shows the results of in vivo anticancer effect test of liposome injection of irinotecan or irinotecan hydrochloride according to the present invention.

Results:

CPT-11 liposome and CPT-11 both inhibited the growth of Ls-174t human colon cancer in nude mice significantly. CPT-11 liposome was dose-dependent in inhibiting the growth of Ls-174t. 4/14 tumor regressed partially when CPT-11 liposome was administrated in high-dose (3 mg/kg). The therapeutic efficacy of CPT-11 liposome was equivalent to CPT-11 (10 mg/kg) when CPT-11 liposome was administrated in low-dose (1 mg/kg). It was indicated that the therapeutic efficacy of CPT-11 liposome may have prompted at least 10 times than the CPT-11 injection. The detailed results were shown in FIG. 3.

What is claimed is:

1. A liposome, comprising:
   irinotecan hydrochloride,
   hydrogenated soybean phosphatidylcholine,
   polyethylene glycol 2000-distearoyl phosphatidyl ethanolamine,
   cholesterol, and
   ethylene diamine tetraacetic acid disodium,
   wherein the weight ratio of the cholesterol to the hydrogenated soybean phosphatidylcholine is about 1:4, and there is no significant change in the particle size and encapsulation efficiency of the liposome after the liposome is stored at 25° C. for 60 days.

2. The liposome according to claim 1, wherein the liposome is prepared by an ion gradient method.

3. The liposome according to claim 2, wherein the liposome has an ion gradient formed between the internal water phase and the external water phase of the liposome.

4. The liposome according to claim 1, wherein the weight ratio of the polyethylene glycol 2000-distearoyl phosphatidyl ethanolamine to the irinotecan hydrochloride is 0.2 to 0.4.

5. A liposome injection comprising the liposome of irinotecan hydrochloride according to claim 1.

6. The liposome according to claim 1, wherein the weight ratio of the hydrogenated soybean phosphatidylcholine to the irinotecan hydrochloride is 2.5:1 to 4:1.

7. The liposome according to claim 3, wherein the internal water phase of the liposome has a higher ion concentration than the external water phase of the liposome.

8. A method of preparing a liposome of irinotecan hydrochloride, comprising:
   1) preparing a blank liposome comprising a neutral phospholipid, polyethylene glycol 2000-distearoyl phosphatidyl ethanolamine, and cholesterol, wherein the weight ratio of the cholesterol to the neutral phospholipid is 1:4, and the neutral phospholipid consists of hydrogenated soybean phosphatidylcholine;
   2) replacing the external water phase of the blank liposome with a solution containing ethylene diamine tetraacetic acid disodium and a salt to obtain a blank liposome having an ionic gradient between the internal water phase and the external water phase of the blank liposome;
   3) preparing an aqueous solution of the irinotecan hydrochloride;
   4) mixing the aqueous solution with the blank liposome having the ionic gradient in a dispersion; and
   5) incubating the dispersion with heating and stirring to obtain a preparation comprising the liposome of irinotecan hydrochloride, wherein the weight ratio of the neutral phospholipid to the irinotecan hydrochloride in the liposome is 2:1 to 4:1, and there is no significant change in the particle size and encapsulation efficiency of the liposome after the liposome is stored at 25° C. for 60 days.

9. The method according to claim 8, further comprising:
   6) removing non-encapsulated irinotecan hydrochloride from the preparation comprising the liposome or irinotecan hydrochloride to obtain a preparation with the non-encapsulated irinotecan hydrochloride being removed; and
   7) concentrating the preparation with non-encapsulated irinotecan hydrochloride being removed.

10. The method according to claim 8, wherein the blank liposome has a desired particle size and is prepared using a method selected from the group consisting of methods A, B, C and D:
   A. dissolving the neutral phospholipid and the cholesterol in anhydrous ethanol or a mixed solvent of anhydrous ethanol and tert-butyl alcohol to obtain a solution; mixing the solution with a buffer to obtain a mixture; obtaining a crude blank liposome after removing the ethanol from the mixture through a reduced pressure distillation; and obtaining the blank liposome from the crude blank liposome using at least one of a high-pressure homogenizer and an extrusion equipment;

B. dissolving the neutral phospholipid and the cholesterol in chloroform or a mixed solvent of chloroform and methanol to obtain a solution; forming a lipid film from the solution using rotary evaporation; obtaining a crude blank liposome after hydrating the lipid film with a buffer; and preparing the blank liposome from the crude blank liposome using at least one of a high-pressure homogenizer and an extrusion equipment;

C. mixing the neutral phospholipid, the cholesterol and a buffer to obtain a mixture; preparing the blank liposome from the mixture using at least one of a high-pressure homogenizer and an extrusion equipment; and D. dissolving the neutral phospholipid and the cholesterol in anhydrous ethanol or a mixed solvent of anhydrous ethanol and tert-butyl alcohol to obtain a solution; mixing the solution with a buffer to obtain a mixture; and preparing the blank liposome from the mixture using at least one of a high-pressure homogenizer and an extrusion equipment;

wherein the buffer is selected from the group consisting of a buffer comprising $Na^+$, $K^+$, $Fe^{2+}$, $Ca^{2+}$, $Ba^{2+}$, $Mn^{2+}$, $Mg^{2+}$, $Li^+$, $NH_4^+$, $H^+$ ion salts and a mixture thereof.

11. The liposome injection according to claim 5, wherein the amount of the ethylene diamine tetraacetic acid disodium is more than 0% (w/v), but less than or equal to 0.5% (w/v), of the liposome injection.

12. The liposome injection according to claim 5, wherein the injection is a liquid injection or a lyophilized powder for injection.

13. The liposome injection according to claim 5, wherein the injection comprises an osmotic pressure regulator selected from the group consisting of glucose, sucrose, sorbitol, mannitol, sodium chloride, glycerine, histidine, histidine hydrochloride, glycine, glycine hydrochloride, lysine, serine, glutamic acid, arginine, valine and a mixture thereof; and the amount of the osmotic pressure regulator is more than 0% (w/v), but less than or equal to 5% (w/v), of the liposome injection.

14. The liposome injection according to claim 5, wherein the injection further comprises an antioxidant selected from the group consisting of a water-soluble antioxidant and an oil-soluble antioxidant; wherein the oil-soluble antioxidant is selected from the group consisting of α-tocopherol, α-tocopherol succinate, α-tocopherol acetate and a mixture thereof; the water-soluble antioxidant is selected from the group consisting of ascorbic acid, sodium bisulfite, sodium sulfite, sodium pyrosulfite, L-cysteine and a mixture thereof; and the amount of the antioxidant is more than 0% (w/v), but less than or equal to 0.5% (w/v), of the liposome injection.

15. The liposome injection according to claim 12, wherein the injection is the lyophilized powder for injection comprising a lyoprotectant, and the lyophilized powder is prepared by freeze-drying.

16. The liposome injection according to claim 5, comprising:

| | |
|---|---|
| irinotecan hydrochloride | 1 part by weight; |
| hydrogenated soybean phosphatidylcholine | 3.4-3.8 parts by weight; |
| polyethylene glycol 2000-distearoyl phosphatidyl ethanolamine | 0.34-0.38 part by weight; |
| Cholesterol | 0.8-0.95 part by weight; and |
| ethylene diamine tetraacetic acid disodium | 0.05-0.09 part by weight | wherein the weight ratio of the cholesterol to the hydrogenated soybean phosphatidylcholine is 1:4.

17. A method of preparing a liposome injection comprising a liposome of irinotecan hydrochloride, the method comprising preparing the liposome using the method of claim 8.

18. The method according to claim 17, further comprising:

adjusting the concentration of the irinotecan hydrochloride in the injection, metering the volume of the injection, sterilizing the injection by filtration, filling the sterilized injection to vials and sealing the vials to obtain a liquid injection; or adding a lyoprotectant to the injection, adjusting the concentration of the irinotecan hydrochloride in the injection, metering the volume of the injection, sterilizing the injection by filtration, filling the sterilized injection to vials, sealing the vials, freeze-drying the sealed vials to obtain a lyophilized power for injection.

19. A liposome, consisting essentially of:
irinotecan hydrochloride,
hydrogenated soybean phosphatidylcholine,
polyethylene glycol 2000-distearoyl phosphatidyl ethanolamine,
cholesterol,
ethylene diamine tetraacetic acid disodium,
ammonium sulfate
injectable water, and
one or more salts
wherein the weight ratio of the cholesterol to the hydrogenated soybean phosphatidylcholine is about 1:4, and
there is no significant change in the particle size and encapsulation efficiency of the liposome after the liposome is stored at 25° C. for 60 days.

20. The liposome of claim 19, wherein the weight ratio of the hydrogenated soybean phosphatidylcholine to the irinotecan hydrochloride is 2.5:1 to 4:1.

21. The liposome of claim 20, wherein the weight ratio of the polyethylene glycol 2000-distearoyl phosphatidyl ethanolamine to the irinotecan hydrochloride is 0.2 to 0.4.

22. A method of treating a tumor in a subject in need thereof, comprising administering to the subject an effective amount of the liposome of claim 1.

23. A method of treating a tumor in a subject in need thereof, comprising administering to the subject an effective amount of the liposome of claim 19.

* * * * *